(12) United States Patent
Liphardt et al.

(10) Patent No.: US 7,477,388 B1
(45) Date of Patent: Jan. 13, 2009

(54) SAMPLE MASKING IN ELLIPSOMETER AND THE LIKE SYSTEMS INCLUDING DETECTION OF SUBSTRATE BACKSIDE REFLECTIONS

(75) Inventors: Martin M. Liphardt, Lincoln, NE (US);
James D. Welch, Omaha, NE (US);
Corey L. Bungay, Lincoln, NE (US);
John A. Woollam, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 336 days.

(21) Appl. No.: 11/439,491

(22) Filed: May 24, 2006

Related U.S. Application Data

(63) Continuation-in-part of application No. 10/731,202, filed on Dec. 10, 2003, now abandoned, and a continuation-in-part of application No. 11/288,785, filed on Nov. 30, 2005, now Pat. No. 7,385,698, and a continuation-in-part of application No. 11/098,669, filed on Apr. 2, 2005, now Pat. No. 7,239,391, and a continuation-in-part of application No. 10/238,241, filed on Sep. 10, 2002, now Pat. No. 6,937,341, and a continuation-in-part of application No. 10/194,881, filed on Jul. 15, 2002, now Pat. No. 6,940,595, and a continuation-in-part of application No. 09/756,515, filed on Jan. 9, 2001, now Pat. No. 6,455,853, and a continuation-in-part of application No. 09/916,836, filed on Jul. 27, 2001, now Pat. No. 6,636,309.

(60) Provisional application No. 60/452,673, filed on Mar. 10, 2003, provisional application No. 60/639,097, filed on Dec. 27, 2004.

(51) Int. Cl.
*G01J 4/00* (2006.01)

(52) U.S. Cl. .................. 356/364; 356/638; 356/369

(58) Field of Classification Search .................. 356/364, 356/369, 603, 613, 621, 638, 445, 239.7, 356/237.2
See application file for complete search history.

(56) References Cited

U.S. PATENT DOCUMENTS

| | | | |
|---|---|---|---|
| 3,799,679 A | 3/1974 | Simtco | 356/431 |
| 3,857,637 A | 12/1974 | Obenredder | 356/613 |
| 5,235,457 A | 8/1993 | Lichtman et al. | 359/368 |
| 5,298,974 A | 3/1994 | Chandley | 356/613 |
| 5,510,892 A | 4/1996 | Mitzutani et al. | 356/139.1 |
| 6,088,092 A | 7/2000 | Chen et al. | 356/237.2 |
| 6,088,104 A | 7/2000 | Peterson | 356/600 |
| 6,097,482 A | 8/2000 | Smith et al. | 356/237.1 |

(Continued)

FOREIGN PATENT DOCUMENTS

EP 0481649 4/1992

(Continued)

*Primary Examiner*—L. G Lauchman
(74) *Attorney, Agent, or Firm*—James D. Welch

(57) ABSTRACT

A system and method of preventing substrate backside reflected components in a beam of electromagnetic radiation caused to reflect from the surface of a sample in an ellipsometer or polarimeter system, involving placing a mask adjacent to the surface of the sample which allows electromagnetic radiation to access the sample over only a limited area, wherein the mask can include detector elements for collecting electromagnetic radiation reflected from the sample backside.

20 Claims, 5 Drawing Sheets

Hole ≥ D & ≤ D'
D=2T' Tan(θ)
D'=T' Tan(θ) + 2T Tan(θ') + T" Tan(θ)

U.S. PATENT DOCUMENTS

| | | | |
|---|---|---|---|
| 6,130,749 A | 10/2000 | Meeks | 356/630 |
| 6,166,808 A | 12/2000 | Greve | 356/601 |
| 6,198,533 B1 | 3/2001 | Meeks | 356/630 |
| 6,275,291 B1 | 8/2001 | Abraham et al. | 356/367 |
| 6,392,749 B1 | 5/2002 | Meeks | 356/634 |
| 2002/0113200 A1 | 8/2002 | Hajjar et al. | |

FOREIGN PATENT DOCUMENTS

| | | |
|---|---|---|
| WO | WO 9624034 | 8/1996 |
| WO | WO 2005/088272 A1 | 9/2005 |

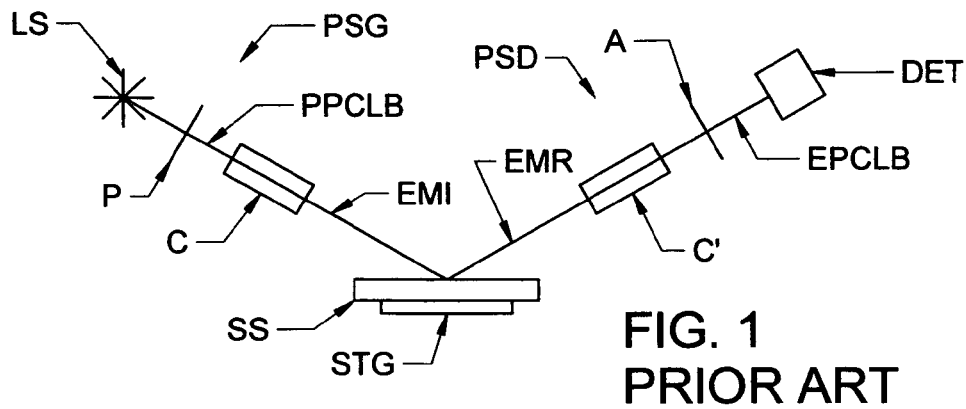
FIG. 1
PRIOR ART
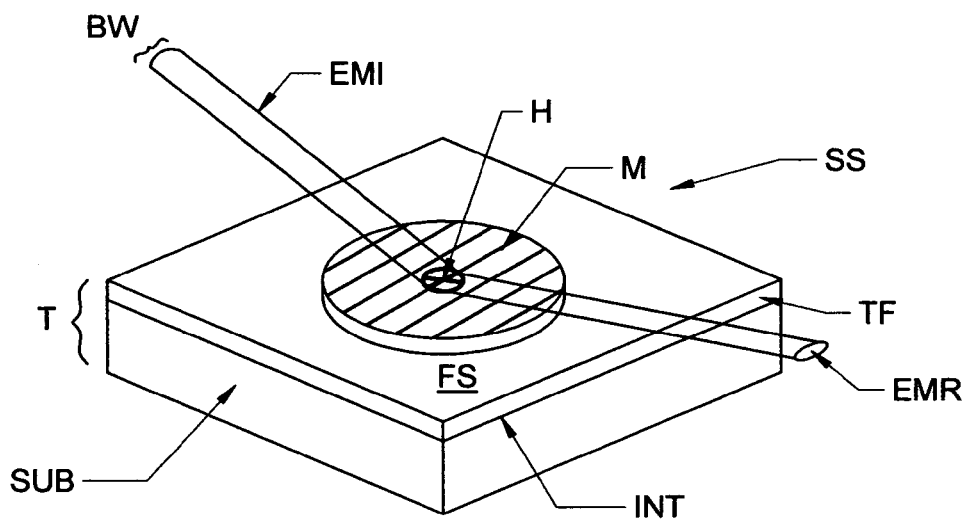
FIG. 2a
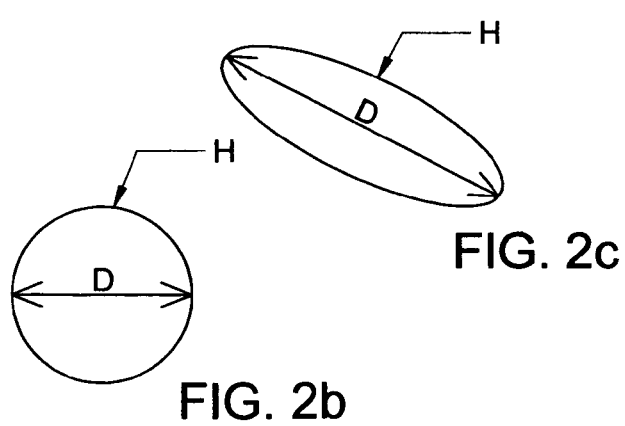
FIG. 2b
FIG. 2c

Hole ≥ D & ≤ D'
D = 2T' Tan(θ)
D' = T' Tan(θ) + 2T Tan(θ') + T" Tan(θ)

D = 2T' Tan(θ)
D" = T' Tan(θ) + 2T'" Tan(θ") + 2T Tan(θ') + T" Tan(θ)
where N2 is compound effect of N layer

SAMPLE MASKING IN ELLIPSOMETER AND THE LIKE SYSTEMS INCLUDING DETECTION OF SUBSTRATE BACKSIDE REFLECTIONS

This application is a CIP of application Ser. No. 10/731,202 Filed Dec. 10, 2003; now abandoned and Claims Benefit of Provisional Application Ser. No. 60/452,673 Filed Mar. 10, 2003 therevia.

This application is further a CIP of application Ser. No. 11/288,785 Filed Nov. 30, 2005 now U.S. Pat. No. 7,385,698, and therevia of application Ser. No. 11/098,669 Filed Apr. 2, 2005 now U.S. Pat. No. 7,239,391, and therevia of the following:

Ser. No. 10/238,241, Filed Sep. 10, 2002, (now U.S. Pat. No. 6,937,341);
   Ser. No. 10/194,881, Filed Jul. 15, 2002, (now U.S. Pat. No. 6,940,595);
   Ser. No. 09/756,515, Filed Jan. 9, 2001, (U.S. Pat. No. 6,455,853);
   Ser. No. 09/916,836, Filed Jul. 27, 2001, (now U.S. Pat. No. 6,636,309);

and via application Ser. No. 11/098,669, Claims benefit of Provisional Application Ser. No. 60/639,097 Filed Dec. 27, 2004).

TECHNICAL AREA

The disclosed invention relates to the use of electromagnetic radiation to investigate samples, and more particularly to the placing of an electromagnetic radiation absorbing and/or scattering and/or reflecting, (in a direction not parallel to electromagnetic radiation provided by an ellipsometer or polarimeter system which is reflected from the sample surface), mask adjacent to a sample, which mask allows electromagnetic radiation to access the sample over only a limited area determined by angle of incidence, sample thickness mask setoff from the sample surface, and ambient, surface film(s) and substrate refractive indices.

BACKGROUND

It is known in ellipsometry and polarimetry to impinge electromagnetic radiation onto a sample at an oblique angle, and collect electromagnetic radiation which reflects from the sample, then via detected change in the polarization state determine properties of the sample. Ellipsometer and Polarimeter Systems sequentially comprise a Source of a beam electromagnetic radiation, a Polarizer element, optionally a compensator element, a sample system, optionally a compensator element, an Analyzer element and a Detector System. It is noted that presence of at least one compensator is a distinguishing factor between ellipsometer and polarimeter systems.

The elements identified as a source of electromagnetic radiation, the polarizer and the sequentially first optional compensator can be considered to form, as a group, a Polarization State Generator (ie. PSG), and the sequentially second optional compensator, analyzer and detector can be considered, as a group, to form a Polarization State Detector (ie. PSD).

A problem which occurs in practicing ellipsometry or polarimetry, where a sample being investigated is not effectively infinitely thick, is that detected electromagnetic radiation which reflects from a sample includes components which reflect not only from the actual sample surface, and perhaps interfaces between thin films thereupon, but also from the back side of the substrate. Said reflection from the substrate backside confuses interpretation of the results, and while such can be accounted for in a mathematical model of the sample, it is often preferable to block said backside reflections and avoid the confusing effects thereof.

One approach to preventing backside reflections is to physically roughen the backside, however this approach alters the sample. The invention disclosed herein provides a simple approach to avoiding the effect of backside reflections without requiring sample modification.

With the present invention in mind a Search was conducted for patents that disclose means for blocking backside reflections from entering a detector. Patent Application No. 2002/0113200 A1 was identified as an aperture 103A is disclosed which can be placed near a detector to block entry of one of two beams from different sources. U.S. Pat. No. 3,799,679 to Simko is disclosed as an iris (38) is present near a detector which can be adjusted to block entry of backside reflection thereinto. Patents to Meeks, U.S. Pat. Nos. 6,130,749, 6,198,533 and 6,392,749 are disclosed for the presence of a hole 2022 in an integrating sphere near, but not atop a sample. U.S. Pat. No. 6,088,092 to Chen et al. is disclosed as it applies a spatial filter (28) to block backside reflection entry into a detector. U.S. Pat. No. 6,088,104 to Peterson is disclosed as a blocking element (B) is present which can be used to block electromagnetic radiation entry to a detector. U.S. Pat. No. 6,097,482 to Smith et al. is disclosed as it applies baffles to block light entry to a detector. U.S. Pat. No. 6,166,808 to Greve is disclosed as it describes use of an aperture near a detector to block backside reflections entry to a detector. A U.S. Pat. No. 3,857,637 to Obenredder, was identified by the Examiner in prosecution of the Parent application hereto, Ser. No, 10/731,202. It is noted that the opaque element (35) therein is shown in FIG. 3 thereof to be offset from contact with the top surface (29) of the sample glass (21). Further, in Col. 6, Lines 45-51 of the 637 patent it is stated that . . . an opaque member (35) such as a metal washer may be positioned adjacent the top surface (see FIGS. 2 and 3). In the instance where the washer is used, it would be advantageously positioned in the return tube (107) to shield the detector surface from the beam reflected from the bottom surface of the glass. However, said 637 patent does not identify or suggest applying such a mask in Ellipsometer and the like systems.

U.S. Pat. No. 5,298,974 to Chandley describes an apparatus for determining the surface topology of an article. FIG. 2 thereof suggests that a Mask-like element with a silt (5) therein can be placed into direct contact with a flat transparent article for the purpose of blocking reflections of an electromagnetic beam from the surface thereof other than those from the surface of the article. Said 974 patent does not identify or suggest applying such a mask in Ellipsometer and the like systems.

Another Published Application is WO 2005/088272A1 by Nanofilm Technologie. This publication is likely the best art found, and discloses blocking electromagnetic radiation backside reflections from a sample by a Mask which is offset from the surface of said sample, in an ellipsometer system. Also, U.S. Pat. No. 3,857,637 describes use of a mask offset from a sample in a non-ellipsometric setting and was cited by the Examiner in prosecution of the Parent application Ser. No. 10/731,202, which it is noted, in contrast, Claims a mask placed directly on the surface of a sample.

In addition, with the present invention in mind, it is further disclosed that Co-Pending application Ser. No. 11/288,785 from which this application is a CIP, is included herein by reference.

Even in view of the known prior art, need remains for a simple to practice method for avoiding effects of sample backside reflections which does not require sample, or investigating system alteration.

DISCLOSURE OF THE INVENTION

As described in Parent application Ser. No. 10/731,202, the disclosed invention is basically a method of investigating a sample system (SS) which typically comprises at least one thin film (TF) on the surface of a substrate (SUB), using a beam of electromagnetic radiation (EMI) which impinges thereupon at an oblique angle of incidence (O). Said method eliminates the effects of reflection from the backside (BS) of said substrate (SUB) in a beam of electromagnetic radiation (EMR) which reflects from the surface (SUR) of the substrate (SUB), or at least one thin film (TF) thereon.

One recitation of the present invention method provides that it is a method of investigating a sample which comprises a sample system (SS) having:
front (FS) and back (BS) sides, with a beam of electromagnetic radiation (EMI) which impinges upon said front side (FS) thereof at an oblique angle of incidence (O). Said method eliminates the effects of reflection from the back side (BS) of said sample system (SS) in a beam of electromagnetic radiation (EMR) which reflects from the front side of said sample system (SS) and comprises:
providing an ellipsometer or polarimeter comprising:
a. a source of a beam electromagnetic radiation (LS);
b. a polarizer element (P);
c. optionally a compensator element (C);
d. a sample system (SS);
e. optionally a compensator element (C');
f. an analyzer element (A); and
g. a detector System (DET);

said sample system (SS) comprising a substrate (SUB) with a surface (SUR) on the front side thereof. This is followed by placing a mask (M) adjacent to surface (SUR) of said front side of said sample system (SS), said mask (M) having a hole (H) therein with an effective diameter (D) which is related to the thickness (T) of the substrate by the equation:

$$D >= 2T \, \text{TAN}(\theta); \text{ and}$$

$$D <= T \, \text{Tan}(\theta) + 2T \, \text{Tan}(\theta') + T \, \text{Tan}(\theta);$$

where T' is the combined thickness of the mask (M) and its offset (T") from the surface of said sample system (SS) and (O) is said oblique angle of incidence at which said beam of electromagnetic radiation (EMI) impinges upon said front side (BS) of said sample system (SS), and where (T) is the thickness of said sample system (SS) and (θ') is an oblique angle of incidence at which said beam of electromagnetic radiation (EMI) impinges upon said back side (BS) of said sample system (SS). The method proceeds by causing an incident beam of electromagnetic radiation (EMI) provided by said source of a beam electromagnetic radiation (LS), to pass through said polarizer (P) and impinge upon the surface (SUR) of the front side of said sample system (SS) at an oblique angle of incidence (O), such that said incident electromagnetic beam (EMI) reflects from the surface (SUR) of said front side of said sample system (SS) as reflected electromagnetic beam (EMR) and then passes through said analyzer (A) and enters said detector (DET), said reflected electromagnetic beam (EMR) having no component therein which reflected from the back side (BS) of said sample system (SS) as a result of the blocking thereof by said mask (M). The method continues with causing said reflected beam of electromagnetic radiation (EMR) which enters said detector (DET) to be analyzed.

Another recitation of the present invention method of investigating a sample system (SS) having:
front (FS) and back (BS) sides and which comprises at least one thin film (TF) on the front side of a substrate (SUB), with a beam of electromagnetic radiation (EMI) which impinges upon a surface (SUR) of said thin film at an oblique angle of incidence (O), said method eliminating the effects of reflection from the back side (BS) of said substrate (SUB) in a beam of electromagnetic radiation (EMR) which reflects from the surface (SUR) of the at least one thin film (TF) comprises:
providing an ellipsometer or polarimeter comprising:
a. a source of a beam electromagnetic radiation (LS);
b. a polarizer element (P);
c. optionally a compensator element (C);
d. a sample system (SS);
e. optionally a compensator element (C');
f. an analyzer element (A); and
g. a detector System (DET);

wherein said sample system comprises a substrate (SUB) with at least one thin film (TF) on the front side thereof, said at least one thin film (TF) presenting with said surface (SUR). The method proceeds with the placing of a mask (M) adjacent to said surface (SUR) of said at least one thin film (TF), said mask having a hole (H) therein with an effective Diameter (D) which is related to the thickness (T) of the sample by the equation:

$$D >= 2T \, \text{TAN}(\theta); \text{ and}$$

$$D <= T \, \text{Tan}(\theta) + 2T''' \, \text{Tan}(\theta'') + 2T \, \text{Tan}(\theta') + T' \, \text{Tan}(\theta)$$

where (T') comprises the combined thickness said mask (M) and its offset (T") from the surface of said at least one thin film (TF) and (θ) is the oblique angle of incidence at which said beam of electromagnetic radiation (EMI) impinges upon said surface (SUR) of said thin film (TF), and where (T) is the thickness of said substrate (SUB) and (θ') is an oblique angle of incidence at which said beam of electromagnetic radiation (EMI) impinges upon said back side of said sample, and where T''' is the thickness of the at least one thin film (TF) and (θ') is an oblique angle at which the beam of electromagnetic radiation which is reflected from the backside (BS) of said substrate makes in said thin film (TF), at the interface between said substrate (SUB) and thin film (TF). Next an incident beam of electromagnetic radiation (EMI) provided by said source of a beam electromagnetic radiation (LS), is caused to pass through said polarizer (P) and impinge upon the sample thin film surface (SUR) at an oblique angle of incidence (O), such that said incident electromagnetic beam (EMI) reflects from the surface (SUR) of said at least one thin film (TF) as reflected electromagnetic beam (EMR) and then passes through said analyzer (A) and enters said detector (DET), said reflected electromagnetic beam (EMR), having no component therein which reflected from the back side (BS) of said substrate (SUB) as a result of the blocking thereof by said mask (M). Said method further involves causing said reflected beam of electromagnetic radiation (EMR) which enters said detector (DET) to be analyzed.

The just recited method can be applied where said at least one thin film comprises a plurality of thin films and wherein (T''') is a composite thin film (TF) thickness and wherein (O'') is an effective oblique angle at which the beam of electromagnetic radiation which is reflected from the backside (BS) of said substrate makes in said thin film (TF), at the interface between said substrate (SUB) and said composite thin film (TF).

Another recitation of the present invention method of investigating a sample which comprises a substrate (SUB) having:
   front (FS) and back (BS) sides, with a beam of electromagnetic radiation (EMI) which impinges upon said front side (FS) thereof at an oblique angle of incidence (O), said method eliminating the effects of reflection from the back side (BS) of said substrate (SUB) in a beam of electromagnetic radiation (EMR) which reflects from the front side of said substrate (SUB), comprises:
   providing an ellipsometer or polarimeter comprising:
   a. a source of a beam electromagnetic radiation (LS);
   b. a polarizer element (P);
   c. optionally a compensator element (C);
   d. a sample system (SS);
   e. optionally a compensator element (C');
   f. an analyzer element (A); and
   g. a detector System (DET);

said sample system (SS) comprising a substrate (SUB) with a surface (SUR) on the front side thereof. Said method proceeds with the placing of a mask (M) on the surface (SUR) of said front side of said substrate (SUB), said mask (M) having a hole (H) therein with an effective diameter (D) which is related to the thickness (T) of the substrate by the equation:

$$D<=2T \text{TAN}(\theta'); \text{ and}$$

where T is the thickness of the sample (SS) and (O') is said oblique angle of incidence at which said beam of electromagnetic radiation (EMI) impinges upon said back side (BS) of said substrate (SUB). This is followed with causing an incident beam of electromagnetic radiation (EMI) of cross sectional diameter (BW), provided by said source of a beam electromagnetic radiation (LS), to pass through said polarizer (P) and impinge upon the surface (SUR) of the front side of said substrate (SUB) at an oblique angle of incidence ($\theta$), such that said incident electromagnetic beam (EMI) reflects from the surface (SUR) of said front side of said substrate (SUB) as reflected electromagnetic beam (EMR) and then passes through said analyzer (A) and enters said detector (DET), said reflected electromagnetic beam (EMR) having no component therein which reflected from the back side (BS) of said substrate (SUB) as a result of the blocking thereof by said mask (M). Again, said method involves causing said reflected beam of electromagnetic radiation (EMR) which enters said detector (DET) to be analyzed.

It is noted that said sample (SS) can be a composite comprising a thin film (TF) on the surface of a substrate (SUB).

In any of the foregoing methods the hole (H) in the mask can be of a shape selected from the group of:
   circular; and
   slit shaped.

Continuing, a present invention system for investigating a sample (SS) having:
   front (FS) and back (BS) sides, with a beam of electromagnetic radiation (EMI) which impinges upon said front side (FS) thereof at an oblique angle of incidence ($\theta$) can comprise:

a mask (M) having top and bottom sides;
   a sample system (SS); and
   a detector (DET);

wherein said mask (M) further comprising detector means (BDETS) on said bottom side thereof facing said front side (FS) of said sample system (SS). Said mask (M), sample system (SS) and detector (DET) are oriented such that the bottom side of said mask (M) is placed adjacent to said front side (FS) of said sample system (SS), said mask (M) having a hole (H) therein with an effective diameter (D) which is related to the thickness (T) of the substrate by the equation:

$$D>=2T \text{ TAN}(\theta); \text{ and}$$

$$D<=T \text{ Tan}(\theta)+2T \text{ Tan}(\theta')+T'' \text{ Tan}(\theta);$$

where T' is the combined thickness of the mask (M) and its offset (T'') from the front side (FS) of said sample (SS) and (O) is said oblique angle of incidence at which said beam of electromagnetic radiation (EMI) impinges upon said front side (BS) of said substrate (SUB), and where (T) is the thickness of said substrate (SUB) and ($\theta'$) is an oblique angle of incidence at which said beam of electromagnetic radiation (EMI) impinges upon said back side (BS) of said substrate (SUB). In use an incident beam of electromagnetic radiation (EMI) is caused to impinge upon the surface (SUR) of the front side (FS) of said sample system (SS) at an oblique angle of incidence ($\theta$), such that said incident electromagnetic beam (EMI) reflects from the surface (SUR) of said front side (FS) of said sample system (SS) as reflected electromagnetic beam (EMR) and enters a detector (DET), said reflected electromagnetic beam (EMR) having no component therein which reflected from the back side (BS) of said substrate (SUB) as a result of the blocking thereof by said mask (M). Importantly, note that components of electromagnetic radiation reflected from the backside (BS) of said sample system (SS), entered said detector means (BDETS) on said bottom side of said mask (M). It is further noted that said system can be an ellipsometer or polarimeter comprising:
   a. a source of a beam electromagnetic radiation (LS) for providing said beam of electromagnetic radiation (EMI) of cross sectional diameter (BW);
   b. a polarizer element (P);
   c. optionally a compensator element (C);

positioned before said sample (SS); and after said sample (SS) there being:
   d. optionally a compensator element (C');
   e. an analyzer element (A); and
   f. a detector System (DET).

A present invention method of investigating a sample (SS) which comprises a substrate (SUB), said sample system (SS) having:
   front (FS) and back (BS) sides, with a beam of electromagnetic radiation (EMI) which impinges upon said front side (FS) thereof at an oblique angle of incidence (O), said method eliminating the effects of reflection from the back side (BS) of said sample system (SS) in a beam of electromagnetic radiation (EMR) which reflects from the front side of said sample system (SS), can utilize the just recited system and comprise:
   providing a mask (M) comprising top and bottom sides, there being detector means (BDETS) on said bottom side thereof;
   placing the bottom side of said mask (M) adjacent to said front side (FS) of said sample system (SS), said mask (M)

having a hole (H) therein with an effective diameter (D) which is related to the thickness (T) of the substrate by the equation:

$$D >= 2T\ \text{TAN}(\theta);\ \text{and}$$

$$D <= T\ \text{Tan}(\theta) + 2T\ \text{Tan}(\theta') + T\ \text{Tan}(\theta);$$

where T' is the combined thickness of the mask and its offset (T") from the surface of said sample (SS) and (O) is said oblique angle of incidence at which said beam of electromagnetic radiation (EMI) impinges upon said front side (BS) of said substrate (SUB), and where (T) is the thickness of said substrate (SUB) and (θ') is an oblique angle of incidence at which said beam of electromagnetic radiation (EMI) impinges upon said back side (BS) of said substrate (SUB). Said method proceeds with the causing of an incident beam of electromagnetic radiation (EMI) of cross sectional diameter (BW) to impinge upon the surface (SUR) of the front side (FS) of said substrate (SUB) at an oblique angle of incidence (θ), such that said incident electromagnetic beam (EMI) reflects from the surface (SUR) of said front side (FS) of said substrate (SUB) as reflected electromagnetic beam (EMR) and enters a detector (DET), said reflected electromagnetic beam (EMR) having no component therein which reflected from the back side (BS) of said sample system (SS) as a result of being blocked by said mask (M). Components of electromagnetic radiation reflected from the backside (BS) of said sample system (SS) enter said detector means (BDETS) on said bottom side of said mask (M). Said method further comprises:

causing at least one selection from the group comprising:
    said reflected beam of electromagnetic radiation (EMR) which enters said detector (DET); and
    at least some of said components of electromagnetic radiation reflected from the backside of said substrate (SUB) which enter said detector means (BDETS)

to be analyzed.

Again said sample can comprise a thin film (TF) on the front side (FS) said substrate (SUB), and the hole (H) in the mask (M) can be of any functional shape, such as circular or slit shaped. Said shapes are functionally equivalent for the purposes of the present invention and are both included in the language "effective diameter".

The invention will be better understood by reference to the Detailed Description Section of the Specification, in conjunction with the Drawings.

SUMMARY

It is therefore a primary purpose and/or objective of the disclosed invention to, in the context of ellipsometer and polarimeter systems, teach a simple system, and method of its application to block reflections from the backside of a sample from reaching a detector, which reflections result from a beam of electromagnetic radiation impinging upon said sample surface at an oblique angle.

It is a further primary purpose and/or objective of the disclosed invention to teach a simple system, and method of its application which enable separate detection of reflections that result from a beam of electromagnetic radiation impinging upon said sample surface at an oblique angle, and which reflect from either the front or back side.

Additional purposes and/or objectives of the disclosed invention will become apparent from a reading of the Specification and Claims.

BRIEF DESCRIPTION OF THE DRAWINGS

FIG. 1 shows a basic prior art Ellipsometer or Polarimeter System.

FIG. 2a demonstrates a system containing a sample for practicing the disclosed invention including a Mask with Hole (H) present therein.

FIGS. 2b and 2c show what are to be considered functionally equivalent Hole (H) shapes.

DETAILED DISCLOSURE

Turning now to the Drawings, there is shown in FIG. 1 a basic prior art Ellipsometer or Polarimeter System comprising a Source (LS) of Electromagnetic Radiation and a Detector (DET). A beam of electromagnetic radiation is shown reflecting from a Sample System (SS). In more detail FIG. 1 shows:
  a. a Source of a beam electromagnetic radiation (LS);
  b. a Polarizer element (P);
  c. optionally a compensator element (C);
  d. a sample system (SS);
  e. optionally a compensator element (C');
  f. an Analyzer element (A); and
  g. a Detector System (DET).

The elements identified as (LS), (P) and (C) can be considered to form, as a group, a Polarization State Generator (PSG), and the components (C'), (A) and (DET) can be considered, as a group, to form a Polarization State Detector (PSD).

Turning now to FIG. 2a, there is demonstrated a solution to blocking electromagnetic radiation reflection (EMR) from the backside (BS) of a Sample System comprising a substrate (SUB), is to place a mask (M) atop thereof. FIG. 2a realistically indicates the presence of a thin film(s) (TF) on the surface (SUR) of the substrate, (which sample comprises (SUB)+(TF)), which mask (M) is made of a material which scatters electromagnetic radiation which is impinged thereupon. Note that the mask (M) has a hole (H) therein through which electromagnetic radiation (EMI) can access the sample. If the hole (H) is of an effective diameter which is smaller than some value based upon the total thickness (T) of the thin film (TM)+the substrate (SUB), then all backside (BS) originated reflections are blocked in the reflected beam (EMR). This is the case whether the electromagnetic radiation is a beam (EMI) has an effective diameter larger or smaller than the effective hole (H) diameter. FIGS. 2b and 2c demonstrate that the Hole (H) can functionally be circular or a slit shape. Said shapes, and other workable shapes, are functionally equivalent for the purposes of the present invention, and are included in the language "effective diameter".

Figure 3A:
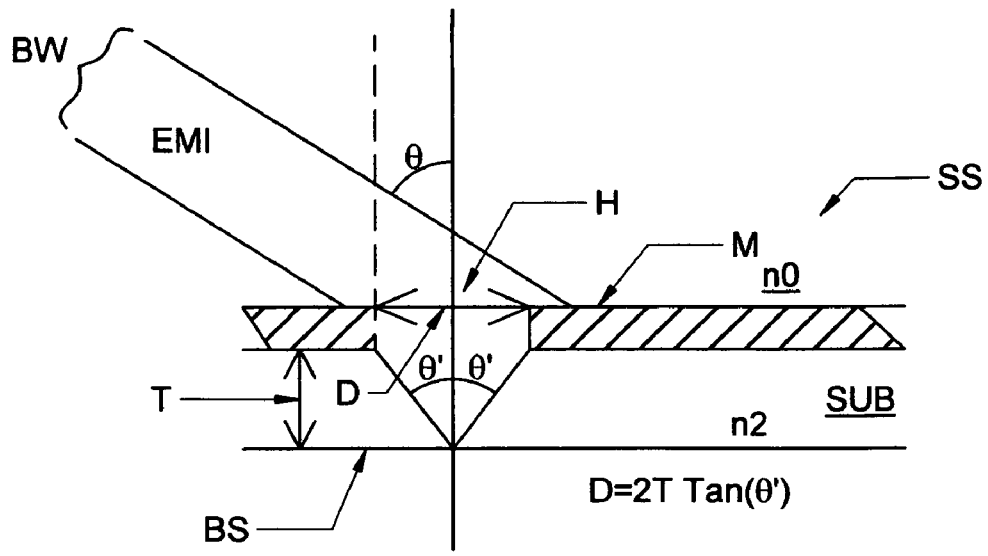
FIG. 3a shows the relationship between the thickness (T) of a sample and the diameter (D) of the hole in the mask (M) placed in contact with the sample surface necessary to block reflections from the backside (BS) of the substrate (SUB).
Figure 3B:
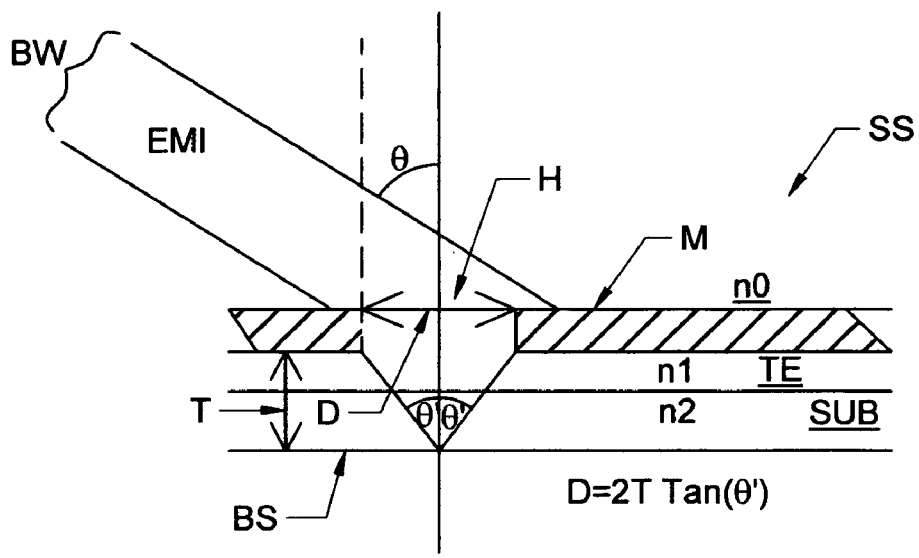
FIG. 3b shows the relationship between the thickness (T) of a sample including at least one thin film (TF) on the surface thereof, and the diameter (D) of the hole in the mask (M) placed in contact with the thin film surface necessary to block reflections from the backside (BS) of the substrate (SUB).

FIG. 3a shows the relationship between the thickness (T) of the sample and the diameter (D) of the hole in the mask (M) necessary to block reflections from the backside (BS) of the substrate (SUB). Also indicated are indices of refraction, (n0), (n1) and (n2) for the ambient, thin film (TF) and substrate (SUB) respectively. Formulas which relate the thin film (TF) thickness (T) to the effective diameter of the hole (H) are also shown in FIG. 3a as:

$$D<=2T\,\text{TAN}(\theta'); \text{ and}$$

$$n0'\,\text{SIN}(\theta)=n2\,\text{Sin}(\theta');$$

where n0' is a composite refractive index based on (n0) and any present thin films, exemplified by (n1) in FIG. 3b. That is, while refraction occurs at each interface between ambient and a thin film, or between two thin films, all said effects are to be considered accounted for by the composite refractive index (n0').

FIG. 3b is similar to FIG. 3a, but shows at least one Thin Film (TF) on the surface of the Substrate (SUB). While technically the analysis of said sample system (SS) requires that multiple applications of Snell's Law be applied, the present invention can be considered to utilize a composite effective index of refraction with the Thickness (T) to arrive at an effective Diameter (D). That is FIG. 3b should be understood to indicate the important functional aspects of the trajectory of the refracted input beam (EMI) in the sample system (SS) below the mask (M). As mentioned with regard to FIG. 3a, Snell's law requires that at each interface (INT) where a refractive index changes, (eg. (n0) to (n1) or (n1) to (n2)), the beam locus changes. However, the end result is that there in an angle of incidence (O) of the beam (EMI) with respect to the front side (FS) of the sample (SS) and an effective angle of incidence (O') at which said beam of electromagnetic radiation (EMI) impinges upon said back side (BS) of said sample (SS), the later of which derives from the composite effect of all such interface interactions and is functionally lumped into an equivalent (n0'). To avoid drawing clutter in FIG. 3b changes at each interface are not indicated but should be understood are present in a real sample.

It is also noted that while there is usually some thin film present on any substrate, there need not be any thin film(s) present on the substrate for the described technique to be applicable. That is, the surface of a substrate per se. can be investigated through a mask (M).

Figure 4A:
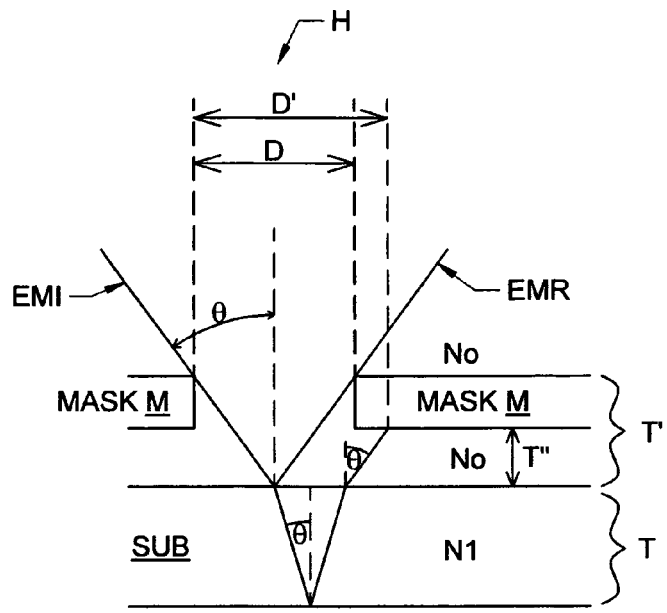
FIG. 4a shows a sample similar to that in FIG. 3a, but in which the mask (M) is offset by a distance (T") from the sample surface (SUR).

FIG. 4a shows a sample similar to that in FIG. 3a, but in which the mask (M) is offset by a distance (T") from the sample surface (SUR). With such a configuration the Diameter (D) of the Hole (H) is provided by a more complex equation and can be within a range indicated by:

$$D>=2T\,\text{TAN}(\theta); \text{ and}$$

$$D<=T\,\text{Tan}(\theta)+2T\,\text{Tan}(\theta')+T\,\text{Tan}(\theta);$$

where T' is the combined thickness of the mask and its offset (T") from the surface of said sample (SS) and (O) is said oblique angle of incidence at which said beam of electromagnetic radiation (EMI) impinges upon said front side (BS) of said substrate (SUB), and where (T) is the thickness of said substrate (SUB) and (θ') is an oblique angle of incidence at which said beam of electromagnetic radiation (EMI) impinges upon said back side (BS) of said substrate (SUB).

Figure 4B:
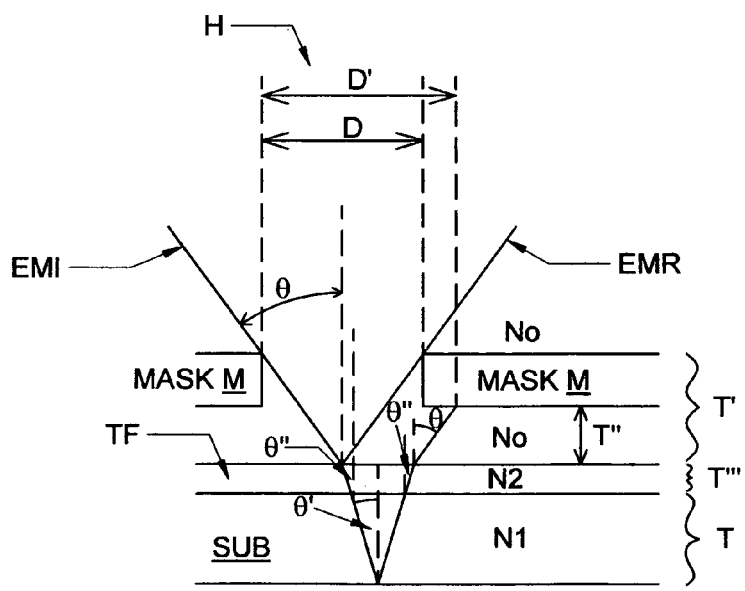
FIG. 4b shows a sample similar to that in FIG. 3b, but in which the mask (M) is offset by a distance (T") from the sample surface (SUR).

FIG. 4b shows a sample similar to that in FIG. 3b and specifically includes indication of at least one Thin Film (TF), however, as in FIG. 4a, the mask (M) is offset by a distance (T") from the surface of the at least one Thin Film (TF). The Diameter (D) of the Hole (H) in the Mask is provided as being within the range:

$$D>=2T\,\text{TAN}(\theta); \text{ and}$$

$$D<=T\,\text{Tan}(\theta)+2T'''\,\text{Tan}(\theta'')+2T\,\text{Tan}(\theta')+T''\,\text{Tan}(\theta);$$

where (T') comprises the combined thickness said mask (M) and its offset (T") from the surface of said at least one thin film (TF) and (θ) is the oblique angle of incidence at which said beam of electromagnetic radiation (EMI) impinges upon said surface (SUR) of said thin film (TF), and where (T) is the thickness of said substrate (SUB) and (θ') is an oblique angle of incidence at which said beam of electromagnetic radiation (EMI) impinges upon said back side of said sample, and where T''' is the thickness of the at least one thin film (TF) and (θ") is an oblique angle at which the beam of electromagnetic radiation which is reflected from the backside (BS) of said substrate makes in said thin film (TF), at the interface between said substrate (SUB) and thin film (TF).

Note that while not shown in FIGS. 4a and 4b to reduce clutter, the Beam will have a Width (BW) which is typically larger than the Hole (H) Diameter (D), as indicated in FIGS. 3a and 3b.

Figure 5A:
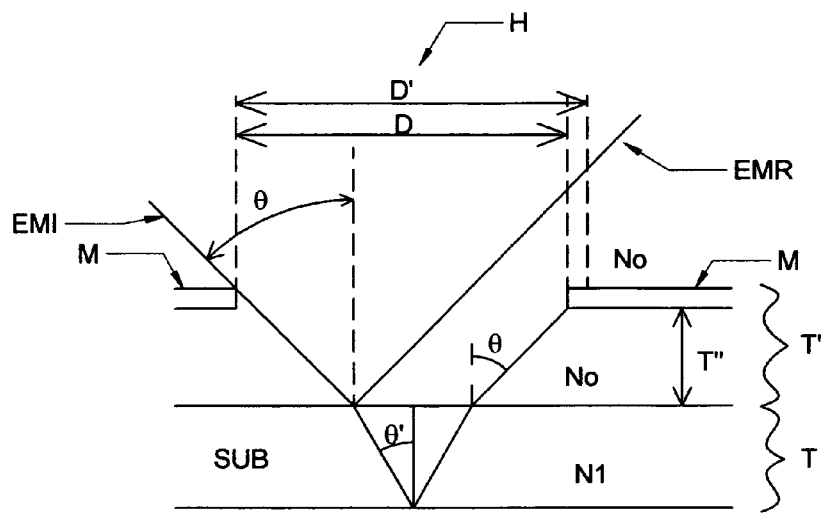
FIG. 5a demonstrates a sample as in FIG. 4a but wherein the mask (M) thickness is small.

FIG. 5a demonstrates a scenario as in FIG. 4a but wherein the mask (M) thickness is small. Note that as the Mask (M) accounts for less of the dimension (T'), (that is (T") accounts for more thereof), that the Hole (H) diameter converges to a single value. That is (D) and (D') become more and more the same value. Of course they will never fully converge to a single value as the mask (M) would then be of no thickness.

Figure 5B:
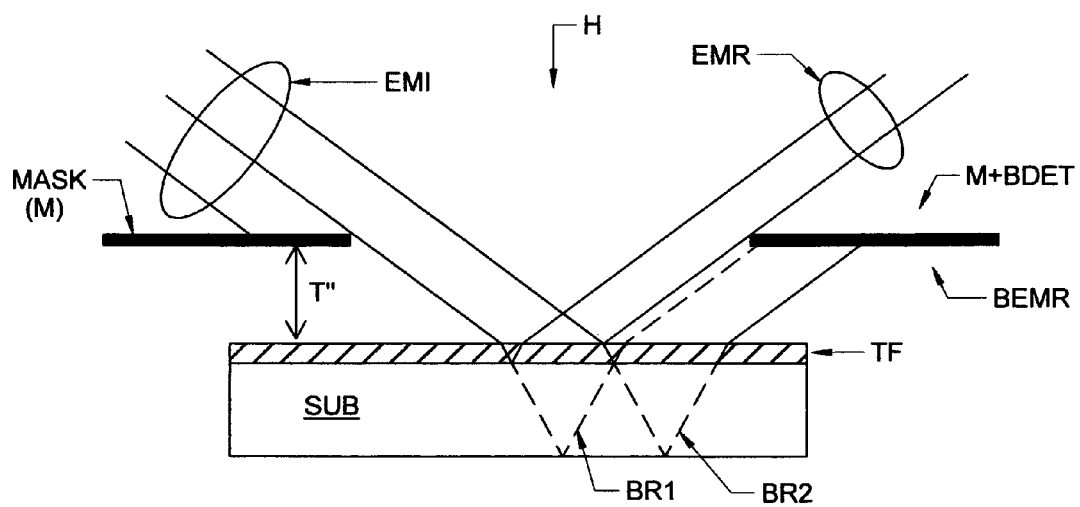
FIG. 5b demonstrates a sample as in FIG. 5a wherein the mask (M) thickness is small, including detail regarding multiple reflections from the backside of the substrate (SUB).

FIG. 5b demonstrates a sample as in FIG. 4b, and a relatively thin Mask (M) as in FIG. 5a. Also shown is detail regarding multiple reflections (BEMR) from the backside of the substrate (SUB) as actually do occur. The new feature in FIG. 5b is the inclusion of a Backside Electromagnetic Radiation Beam Detector (BDET) to form a combination Mask and Backside Electromagnetic Radiation Beam Detector (M+BDET). Said Backside Electromagnetic Radiation Beam Detector enables collection of information contained in Backside Reflections which are lost in a system which only blocks them. Of course the Front Side Reflected Beam (EMR) can still be collected by a conventional detector.

Figure 6A:
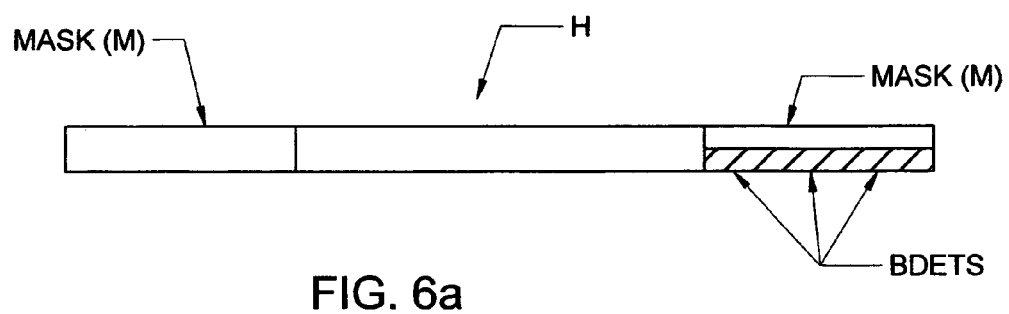
FIGS. 6a and 6b shows that the mask (M) can include backside reflection detector elements (BDETS).
Figure 6B:
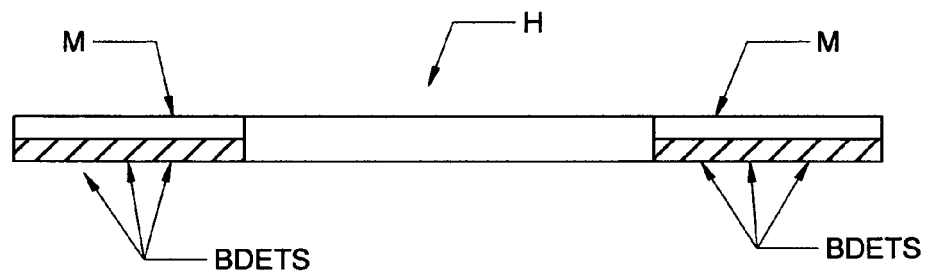

FIGS. 6a and 6b show that the mask (M) can include backside reflection detector elements (BDETS), which can comprise solid state detector elements or the ends of light fibers, for instance, which conduct collected electromagnetic radiation to separate detectors, (not shown).

It is to be understood that as regards the Masking aspect of the present invention, any mask which blocks backside reflections from entering a detector of electromagnetic radiation reflected from the front side of a sample is within the scope of the disclosed invention. Masks can be made of material which is absorbing and/or scattering and/or reflecting of electromagnetic radiation, if in a direction not parallel to the electromagnetic radiation reflected from the substrate surface.

Finally, as regards masks (M) comprising any the hole (H) geometry which are offset from the top surface of a sample by a distance (T"), (see FIGS. 4a, 4b, 5a and 5b), as opposed to being placed directly on said top surface, (see FIGS. 3a and 3b), an Important aspect of the present invention is considered to be the inclusion of backside reflection detector capability present on the underside of the Mask (M).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of investigating a sample which comprises a sample system SS having:
   front FS and back BS sides,
with a beam of electromagnetic radiation EMI which impinges upon said front side FS thereof at an oblique angle of incidence θ, said method eliminating the effects of reflection from the back side BS of said sample system SS in a beam of electromagnetic radiation EMR which reflects from the front side of said sample system SS, said method comprising:
   providing an ellipsometer or polarimeter comprising:
      a) a source of a beam electromagnetic radiation LS;
      b) a polarizer element P;
      c) optionally a compensator element C;
      d) a sample system SS;
      e) optionally a compensator element C';
      f) an analyzer element A; and
      g) a detector System DET;
said sample system SS comprising a substrate SUB with a surface SUR on the front side thereof;
   placing a mask M adjacent to surface SUR of said front side of said sample system SS, said mask M having a hole H therein with an effective diameter D which is by the equations:

$$D >= 2T\ \mathrm{TAN}(\theta);\ \text{and}$$

$$D <= T\ \mathrm{Tan}(\theta) + 2T\ \mathrm{Tan}(\theta') + T''\ \mathrm{Tan}(\theta);$$

where T' is the combined thickness of the mask M and its offset T" from the surface of said sample system SS and θ is said oblique angle of incidence at which said beam of electromagnetic radiation EMI impinges upon said front side BS FS of said sample system SS, and where T is the thickness of said sample system SS and θ' is an oblique angle of incidence at which said beam of electromagnetic radiation EMI impinges upon said back side BS of said sample system SS;
   causing an incident beam of electromagnetic radiation EMI provided by said source of a beam electromagnetic radiation LS, to pass through said polarizer P and impinge upon the surface SUR of the front side of said sample system SS at an oblique angle of incidence θ,
such that said incident electromagnetic beam EMI reflects from the surface SUR of said front side of said sample system SS as reflected electromagnetic beam EMR and then passes through said analyzer A and enters said detector DET, said reflected electromagnetic beam EMR having no component therein which reflected from the back side BS of said sample system SS as a result of the blocking thereof by said mask M; and
   causing said reflected beam of electromagnetic radiation EMR which enters said detector DET to be analyzed.

2. A method of investigating a sample system SS having:
   front FS and back BS sides and which comprises at least one thin film TF on the front side of a substrate SUB,
with a beam of electromagnetic radiation EMI which impinges upon a surface SUR of said thin film at an oblique angle of incidence θ, said method eliminating the effects of reflection from the back side BS of said substrate SUB in a beam of electromagnetic radiation EMR which reflects from the surface SUR of the at least one thin film TF, said method comprising:
   providing an ellipsometer or polarimeter comprising:
      a) a source of a beam electromagnetic radiation LS;
      b) a polarizer element P;
      c) optionally a compensator element C;
      d) a sample system SS;
      e) optionally a compensator element C';
      f) an analyzer element A; and
      g) a detector System DET;
wherein said sample system comprises a substrate SUB with at least one thin film TF on the front side thereof, said at least one thin film TF presenting with said surface SUR, and
   placing a mask M adjacent to said surface SUR of said at least one thin film TF, said mask having a hole H therein with an effective Diameter D which is determined by the equations:

$$D >= 2T\ \mathrm{TAN}(\theta);\ \text{and}$$

$$D <= T\ \mathrm{Tan}(\theta) + 2T'''\ \mathrm{Tan}(\theta'') + 2T\ \mathrm{Tan}(\theta') + T''\ \mathrm{Tan}(\theta)$$

where T' comprises the combined thickness said mask M and its offset T" from the surface of said at least one thin film TF and θ is the oblique angle of incidence at which said beam of electromagnetic radiation EMI impinges upon said surface SUR of said thin film TF, and where T is the thickness of said substrate SUB and θ' is an oblique angle of incidence at which said beam of electromagnetic radiation EMI impinges upon said back side of said sample, and where T''' is the thickness of the at least one thin film TF and θ" is an oblique angle at which the beam of electromagnetic radiation which is reflected from the backside BS of said substrate makes in said thin film TF, at the interface between said substrate SUB and thin film TF;
   causing an incident beam of electromagnetic radiation EMI provided by said source of a beam electromagnetic radiation LS, to pass through said polarizer P and impinge upon the sample thin film surface SUR at an oblique angle of incidence θ;
such that said incident electromagnetic beam EMI reflects from the surface SUR of said at least one thin film TF as reflected electromagnetic beam EMR and then passes through said analyzer A and enters said detector DET, said reflected electromagnetic beam EMR, having no component therein which reflected from the back side BS of said substrate SUB as a result of the blocking thereof by said mask M; and
   causing said reflected beam of electromagnetic radiation EMR which enters said detector DET to be analyzed.

3. A method as in claim 2, in which said at least one thin film comprises a plurality of thin films and wherein (T''') is a composite thin film TF thickness and wherein θ" is an effective oblique angle at which the beam of electromagnetic radiation which is reflected from the backside BS of said substrate makes in said thin film TF, at the interface between said substrate SUB and said composite thin film TF.

4. A method of investigating a sample which comprises a substrate SUB having:
   front FS and back BS sides,
with a beam of electromagnetic radiation EMI which impinges upon said front side FS thereof at an oblique angle of incidence θ, said method eliminating the effects of reflection from the back side BS of said substrate SUB in a beam of electromagnetic radiation EMR which reflects from the front side of said substrate SUB, said method comprising:
   providing an ellipsometer or polarimeter comprising:

a) a source of a beam electromagnetic radiation LS;
b) a polarizer element P;
c) optionally a compensator element C;
d) a sample system SS;
e) optionally a compensator element C';
f) an analyzer element A; and
g) a detector System DET;

said sample system SS comprising a substrate SUB with a surface SUR on the front side thereof;

placing a mask M on the surface SUR of said front side of said substrate SUB, said mask M having a hole H therein with an effective diameter D which is related to the thickness T of the substrate by the equation:

$$D<=2T\,\text{TAN}(\theta'); \text{ and}$$

where T is the thickness of the sample SS and $\theta'$ is said oblique angle of incidence at which said beam of electromagnetic radiation EMI impinges upon said back side BS of said substrate SUB;

causing an incident beam of electromagnetic radiation EMI of cross sectional diameter (BW), provided by said source of a beam electromagnetic radiation LS, to pass through said polarizer P and impinge upon the surface SUR of the front side of said substrate SUB at an oblique angle of incidence $\theta$, such that said incident electromagnetic beam EMI reflects from the surface SUR of said front side of said substrate SUB as reflected electromagnetic beam EMR and then passes through said analyzer A and enters said detector DET, said reflected electromagnetic beam EMR having no component therein which reflected from the back side BS of said substrate SUB as a result of the blocking thereof by said mask M; and causing said reflected beam of electromagnetic radiation EMR which enters said detector DET to be analyzed.

5. A method as in claim 4 in which said sample SS is a composite comprising a thin film TF on the surface of a substrate SUB.

6. A method of investigating a sample having:
  front and back sides and which comprises at least one thin film TF on the front side of a substrate SUB,
with a beam of electromagnetic radiation EMI which impinges upon a surface SUR of said thin film at an oblique angle of incidence $\theta$, said method eliminating the effects of reflection from the back side BS of said substrate SUB in a beam of electromagnetic radiation EMR which reflects from the surface SUR of the at least one thin film TF, said method comprising:
  providing an ellipsometer or polarimeter comprising:
    a) a source of a beam electromagnetic radiation LS;
    b) a polarizer element P;
    c) optionally a compensator element C;
    d) a sample system SS;
    e) optionally a compensator element C';
    f) an analyzer element A; and
    g) a detector System DET;

said sample system SS comprising a substrate SUB with at least one thin-film TF on the front side thereof, said at least one thin film TF presenting with said surface SUR, and
  placing a mask M in direct contact with said surface SUR of the at least one thin film TF, said mask having a hole H therein with an effective radius D which is related to the thickness T of the sample by the equation:

$$D<=2T\,\text{TAN}(\theta);$$

where T is the combined thickness of said at least one thin film TF and the substrate SUB and $\theta'$ is an oblique angle of incidence at which said beam of electromagnetic radiation EMI impinges upon said back side of said sample;

causing an incident beam of electromagnetic radiation EMI provided by said source of a beam electromagnetic radiation LS to impinge upon the sample thin film surface SUR at an oblique angle of incidence $\theta$;

such that said incident electromagnetic beam EMI reflects from the surface SUR of said at least one thin film TF as reflected electromagnetic beam EMR, said reflected electromagnetic beam EMR having no component therein which reflected from the back side BS of said substrate SUB as a result of the blocking thereof by said mask M; and causing said reflected beam of electromagnetic radiation EMR to be analyzed.

7. A method as in claim 1, in which the hole H is of a shape selected from the group of:
  circular; and
  slit shaped.

8. A method as in claim 2, in which the hole H is of a shape selected from the group of:
  circular; and
  slit shaped.

9. A method as in claim 3, in which the hole H is of a shape selected from the group of:
  circular; and
  slit shaped.

10. A method as in claim 4, in which the hole H is of a shape selected from the group of:
  circular; and
  slit shaped.

11. A method as in claim 5, in which the hole H is of a shape selected from the group of:
  circular; and
  slit shaped.

12. A method as in claim 6, in which the hole H is of a shape selected from the group of:
  circular; and
  slit shaped.

13. A method of investigating a sample SS which comprises a substrate SUB, said sample system SS having:
  front FS and back BS sides,
with a beam of electromagnetic radiation EMI which impinges upon said front side FS thereof at an oblique angle of incidence $\theta$, said method eliminating the effects of reflection from the back side BS of said sample system SS in a beam of electromagnetic radiation EMR which reflects from the front side of said sample system SS, said method comprising:
  providing a mask M comprising top and bottom sides, there being detector means BDETS on said bottom side thereof;
  placing the bottom side of said mask M adjacent to said front side FS of said sample system SS, said mask M having a hole H therein with an effective diameter D which is determined the equations:

$$D>=2T\,\text{TAN}(\theta); \text{ and}$$

$$D<=T\,\text{Tan}(\theta)+2T\,\text{Tan}(\theta')+T''\,\text{Tan}(\theta);$$

where T' is the combined thickness of the mask and its offset T'' from the surface of said sample SS and O is said oblique angle of incidence at which said beam of electromagnetic radiation EMI impinges upon said front side BS of said substrate SUB, and where T is the thickness of said substrate SUB and $\theta'$ is an oblique angle of incidence at which said beam of electromagnetic radiation EMI impinges upon said back side BS of said substrate SUB;

causing an incident beam of electromagnetic radiation EMI of cross sectional diameter (BW) to impinge upon the surface SUR of the front side FS of said substrate SUB at an oblique angle of incidence O, such that said incident electromagnetic beam EMI reflects from the surface SUR of said front side FS of said substrate SUB as reflected electromagnetic beam EMR and enters a detector DET, said reflected electromagnetic beam EMR having no component therein which reflected from the back side BS of said sample system SS as a result of being blocked by said mask; and such that components of electromagnetic radiation reflected from the backside BS of said sample system SS enter said detector means BDETS on said bottom side of said mask M;
said method further comprising:
causing at least one selection from the group comprising:
    said reflected beam of electromagnetic radiation EMR which enters said detector DET; and
    at least some of said components of electromagnetic radiation reflected from the backside of said substrate SUB which enter said detector means BDETS
to be analyzed.

14. A method as in claim 13 in which said sample comprises a thin film TF on the front side FS said substrate SUB.

15. A method as in claim 13, in which the hole H is of a shape selected from the group of:
    circular; and
    slit shaped.

16. A method as in claim 13 in which said beam of electromagnetic radiation EMI is provided by an ellipsometer or polarimeter comprising:
    a) a source of a beam electromagnetic radiation LS for providing said beam of electromagnetic radiation EMI of cross sectional diameter (BW);
    b) a polarizer element P;
    c) optionally a compensator element C;
positioned before said sample SS; and after said sample SS there being:
    d) optionally a compensator element C';
    e) an analyzer element A; and
    f) a detector System DET.

17. A system for investigating a sample SS having:
    front FS and back BS sides,
with a beam of electromagnetic radiation EMI which impinges upon said front side FS thereof at an oblique angle of incidence O, said method eliminating the effects of reflection from the back side BS of said sample system SS in a beam of electromagnetic radiation EMR which reflects from the front side of said sample system SS, said system comprising:
    a mask M having top and bottom sides;
    a sample system SS; and
    a detector DET;
said mask M further comprising detector means BDETS on said bottom side thereof facing said front side FS of said sample system SS;
said mask M, sample system SS and detector DET being oriented such that the bottom side of said mask M is placed adjacent to said front side FS of said sample system SS, said mask M having a hole H therein with an effective diameter D which is determined by the equations:

$$D >= 2T\, \text{TAN}(\theta);\ \text{and}$$

$$D <= T\, \text{Tan}(\theta) + 2T\, \text{Tan}(\theta') + T''\, \text{Tan}(\theta);$$

where T' is the combined thickness of the mask M and its offset T'' from the front side FS of said sample SS and $\theta$ is said oblique angle of incidence at which said beam of electromagnetic radiation EMI impinges upon said front side BS of said substrate SUB, and where T is the thickness of said substrate SUB and $\theta'$ is an oblique angle of incidence at which said beam of electromagnetic radiation EMI impinges upon said back side BS of said substrate SUB;

such that in use an incident beam of electromagnetic radiation EMI is caused to impinge upon the surface SUR of the front side FS of said sample system SS at an oblique angle of incidence $\theta$, such that said incident electromagnetic beam EMI reflects from the surface SUR of said front side FS of said sample system SS as reflected electromagnetic beam EMR and enters a detector DET, said reflected electromagnetic beam EMR having no component therein which reflected from the back side BS of said substrate SUB as a result of the blocking thereof by said mask M; and such that components of electromagnetic radiation reflected from the backside BS of said sample system SS, enter said detector means BDETS on said bottom side of said mask M.

18. A method as in claim 17 in which the bottom side of said mask M is placed directly on said front side FS of said sample system SS and in which:

$$T'=\theta;\ \text{and}$$

$$T''=\theta.$$

19. A method as in claim 17 in which said sample SS is a composite comprising a thin film TF on the surface of a substrate SUB.

20. A method as in claim 17, in which the hole H is of a shape selected from the group of:
    circular; and
    slit shaped.

* * * * *